United States Patent [19]
Grollier et al.

[11] Patent Number: 4,767,618
[45] Date of Patent: * Aug. 30, 1988

[54] COSMETIC COMPOSITIONS FOR THE TREATMENT OF THE HAIR AND SKIN CONTAIN IN THE FORM OF A POWDER PARTICLES RESULTING FROM THE PULVERIZATION OF AT LEAST ONE PLANT SUBSTANCE AND A COHESION AGENT

[75] Inventors: Jean-Francois Grollier, Paris; Josiane Allec, Pierrefitte; Chantal Fourcadier, Paris; Georges Rosenbaum, Asnieres; Patrick Darmenton, Villejuif, all of France

[73] Assignee: L'Oreal, Paris, France

[*] Notice: The portion of the term of this patent subsequent to Nov. 9, 1999 has been disclaimed.

[21] Appl. No.: 790,145

[22] Filed: Oct. 22, 1985

Related U.S. Application Data

[62] Division of Ser. No. 352,104, Feb. 25, 1982, Pat. No. 4,569,839.

[30] Foreign Application Priority Data

Feb. 27, 1981 [LU] Luxembourg .......................... 83173

[51] Int. Cl.⁴ ...................... A61K 7/06; A61K 35/78; A61K 7/00

[52] U.S. Cl. .................... 424/74; 424/195.1; 424/70; 424/47; 514/844

[58] Field of Search ................. 424/74, 195.1, 70, 47; 514/844

[56] References Cited

U.S. PATENT DOCUMENTS

| 375,860 | 1/1938 | Worthington | 424/74 |
| 4,128,640 | 12/1978 | Klein | 424/195.1 |
| 4,358,286 | 11/1982 | Grollier et al. | 424/74 |
| 4,459,285 | 7/1984 | Grollier et al. | 424/74 |
| 4,569,839 | 2/1986 | Grollier | 424/74 |
| 4,581,230 | 4/1986 | Grollier et al. | 424/74 |

OTHER PUBLICATIONS

*The Extra Pharmacopia*, pp. 508 and 704 (1936).
Hirschhorn, *The Home Herbal Doctor*, pp. 79–80 (1982).

Primary Examiner—Jerome D. Goldberg
Assistant Examiner—F. L. Krosnick
Attorney, Agent, or Firm—Cushman, Darby & Cushman

[57] ABSTRACT

A cosmetic composition for the treatment of the hair and skin comprises at least 5 weight percent of pulverized particles of at least one plant. The particles have a granulometry lower than 125 microns. The composition also includes a cohesion agent in an amount to maintain the homogeneity of the composition.

4 Claims, No Drawings

COSMETIC COMPOSITIONS FOR THE TREATMENT OF THE HAIR AND SKIN CONTAIN IN THE FORM OF A POWDER PARTICLES RESULTING FROM THE PULVERIZATION OF AT LEAST ONE PLANT SUBSTANCE AND A COHESION AGENT

This is a division of application Ser. No. 352,104, filed Feb. 25, 1982, now U.S. Pat. No. 4,569,839.

The present invention relates to a cosmetic composition for the treatment of the hair and skin, this composition comprising a powder resulting from the pulverization of at least one plant substance and a cohesion agent.

For years both the pharmaceutical industry and the cosmetic industry have employed in numerous formulations active substances resulting from the extraction of plants by different processes such as maceration, digestion, decoction, infusion or lixiviation.

In certain cases and principally in cosmetics, the plants are employed in the form of entire plants applied to the skin, or in a coarsely pulverized form so as to provide cataplasms when diluted with water.

Representative cataplasms include, in particular, those obtained from emollient flour or from henna powder and were used for the coloration of the hair or skin.

These cataplasms exhibit numerous disadvantages caused essentially by coarse grinding of the plants which most often resulted in lumpy cataplasms which were difficult to apply to the skin and hair and which were not easily removed, especially from the hair.

Moreover, these known products were difficult to preserve which prevented them from being made in a ready-to-use form.

It has now been found that it is possible to essentially eliminate or significantly reduce the disadvantages mentioned mentioned above by using powders of pulverized plant substances having a determined granulometry and being combined with a cohesion agent, the definition of which is given below.

The present invention relates to a cosmetic composition for the treatment of the hair and skin containing in the form of a powder at least 5 weight percent of particles resulting from the pulverization of at least one plant substance and having a granulometry less than 125 microns and, preferably, less than 80 microns, and at least one cohesion agent which maintains homogeneity of the composition.

The particularly fine granulometry is obtained by known pulverization methods, such as by grinding or micronization, optionally followed by a sieving operation, this degree of granulometry being critical to the production of compositions exhibiting all the requisite characteristics.

By the expression "cohesion agent" is meant a substance or compound capable:

of avoiding decantation of the finely pulverized plant particles, in solution, of facilitating the spreading of the composition on the skin or hair, of avoiding drying out of the composition where it is exposed to the free air, and of facilitating the removal of the composition from the hair or skin.

The cohesion agent which responds to these criteria can be a solvent, a fatty body, a thickening agent, an emulsifying agent, an emulsion or a mixture thereof.

The plant powder substance used in the composition of the present invention can originate from plants, shrubs or trees or from certain portions such as roots, stems, leaves, flowers, fruits or seeds. These powders can be obtained from diverse varieties of plant substances of which certain ones can exhibit different properties such as emollient properties, anti-inflammatory properties, anti-pruriginous properties, antiseptic properties, antiperspirant properties, astringent properties, soothing properties, cicatrisive properties or tonic properties or even plant substances capable of imparting a color to compositions containing them or capable of coloring the keratin of the hair and skin.

These plant substances as a function of their properties are referenced in the following publications:

(i) R. R. Paris, H. Moyse. *Matiere Medicale*, Vol. 3 (Masson 1965, 1967, 1971)

(ii) G. Garnier, Bezanger, Beauquesne and Debraux, *Resources Medicinales de la Flore Francaise*, (Vigot 1961)

(iii) H. Leclerc. Précis de phytothérapie (Masson 1976)

(iv) G. Fort. *Guide de traitement par les plantes medicinales et phytocosmetologie*, (Heures de France 1976)

(v) L. Bezanger, Beauquesne, M. Pinkas, M. Torck, *Les plantes dans la therapeutie moderne*, (Maloine 1975)

(vi) E. Perrot, R. Paris, *Les plantes medicinales*, (Presses Universitaires 1971)

(vii) J. Valnet, *Phytotherapie*, (Maloine 1976).

As a function of these different properties, (1) those plants exhibiting emollient properties include apricot hee (*Prunus armenica*), cornflower (*Centaurea cyanus*), mullein (Verbascum spp), chamomile (*Anthemis nobilis*), wild chamomile (*Matricaria chamomilla*), red poppy (*Papaver rhoeas*), fenugreek (*Trigonella foenum graceum*), marsh mallow (*Althaea officinalis*), linen (*Linum usitissimum*), white lily (*Lilium candidum*), mallow (Malva spp), marigold (*Calandula officinalis*), elder (*Sambuscus nigra*), lime tree (Tilia spp), colt's-foot (*Tussilage Iarfara*), fleawort (*Plantago psyllium*), plantain (Plantago spp), quince (*Cyclonia vulgaris*), peachtree (*Prunus persica*), sweet orange tree (*Citrus aurantium*), barbary fig (*Opuntia vulgaris*), and apple-tree (*Pirus malus*), (2) those plants exhibiting anti-inflammatory properties include agrimony (*Agrimonia eupatoria*), hawthorn (*Grataegus oxyacantha*), common heather (*Calluna vulgaris*), quick grass (*Agropurum repens*) or Bermuda grass (*Cynodon dactylon*), juniper (*Juniperus communis*), marsh mallow (*Althaea officinalis*), elder (*Sambuscus nigra*), lime tree (Tilia spp), fenugreek (*Trigonella foenum graecum*), gentian (*Gentiana lutea*), lettuce (*Lactuca sativa*), pansy (Viola spp), plantain (Plantago spp), blackberry (*Rubus fruticosus*), rosemary (*Rosmarinus officinalis*), sage (*Salvia officinalis*), black bryony (*Tamus communis*), colt's-foot (*Tussilage Iarfara*), tea (*Camellia theasinensis*), live ever (*Helicrysum arenarium*), and daisy (*Bellis perennis*), (3) those plants exhibiting anti-pruriginous properties include lady's mantel (*Alchemilla vulgaris*), lavender (*Lavandula officinalis*), walnut-tree (Juglon spp), plantain (Plantago spp), Devil's bit scabious (*Scabiosa succisa*), cabbage (*Brassica oleracea*), chervil (*Anthriscus cerefolium*), muermera (*Clematis vitalba*), cucumber (*Cucumis sativus*), black root (*Symphytum officinale*), birthwort (*Aristolochia clematitis*), burdock (*Arctium majus*), mullein (Verbascum spp), chamomile (*Anthemis* nobilis), euphrasy (*Euphrasia rostkowiana*), and ivy (*Hedera helix*), (4) those plants exhibiting antiseptic properties include garlic (*Allium sativum*), agrimony (*Agrimonia eupatoria*), blueberry (*Vaccinium myrtillus*), burdock (*Arctium majus*), chestnut tree (Quercus spp), black root (*Symphytum officinale*), blue-gum (*Eucalyptus globulus*), juniper (*Juniperus communis*), geranium (Geranium spp), oleander (*Nerium oleander*), lavender (*Lavandula officinalis*), marjoram (*Majorana hortensis*), mint (Mentha spp), pine tree (Pinus spp), rosemary (*Rosmarinus officinalis*), sandalwood (Santalum spp), serpollet (*Thymus serpyllum*), garden thyme (*Thymus vulgaris*), sage (*Salvia officinalis*), honey suckle (Conicera spp), live ever (*Helicrysum arenarium*), daisy (*Bellis perennis*), and tansy (*Tanatecum vulgare*), (5) those plants exhibiting antiperspirant properties include: sage (*Salvia officinalis*), chestnut tree (Quercus spp), walnut tree (Juglon spp), pine tree (Pinus spp), horsetail (Equisetum spp), and colt's foot (*Tussilage Iarfara*), (6) those plants exhibiting astringent properties include acacia (*Robinia pseudoacacia*), yarrow (*Achillea Millefolium*), agrimony (*Agrimonia eupatoria*), lady's mantel (*Alchemilla vulgaris*), stawberry tree (*Arbutus unedo*), mugwort (*Artemisia vulgaris*), black root (*Symphytum officinale*), evergreen cypress (*cupressus sempervirens*), chestnut tree (Quercus spp), dog rose (*Rosa canina*), witch-hazel (*Hamamelis virginiana*), black mulberry tree (*Morus nigra*), blueberry (*Vaccinium myrtillus*), common hazel (*Corylus avellana*), walnut tree (Juglon spp), nettle (Urtica spp), poplar (Populus spp), plantain (Plantago spp), blackberry (*Rubus fruticosus*), rhatany (*Krameria triaudra*), French rose (*Rose gallica*), grass-polly (*Lythrum salicaris*), willow (*Silix alba*), tea (*Camellia theasinensis*), tormentil (*Potentilla tormentilla*), vine (*Vitis vinifera*) and melilot (*Melilotus officinalis*), (7) those plants exhibiting soothing properties include carrot (*Daucus carota*), pansy (Viola spp), elder (*Sambuscus nigra*), lime tree (Tilia spp), basil (*Ocimum basilicum*), camphor-tree (*Cinnamonum camphora*), pear tree (*Pyrus communis*), apple-tree (*Pirus malus*), vine (*Vitis vinifera*), lettuce (*Lactuca sativa*) and French rose (*Rose gallica*), passion flower (Possiflora spp)

(8) those plants exhibiting cicatrisive properties include St. John's wort (*Hypericum perforatum*), silverweed (*Potentilla anserina*), marigold (*Calandula officinalis*), wild chamomile (*Matricaria chamomilla*), black root (*Symphytum officinale*), chamomile (*Anthemis nobilis*), yarrow (*Achillea Millefolium*), wormwood (*Artemisia absinthium*), agrimony (*Agrimonia eupatoria*), mugwort (*Artemisia vulgaris*), arnica (*arnica montana*), chervil (*Anthriscus cerefolium*), myrthe (*Myrtus communis*), periwinkle (Vinca spp), plantain (Plantage spp), poplar (Populus spp), cowslip (*Primula officinalis*), sage (*Salvia officinalis*), groundsel (*Senecio vulgaris*), elder (*Sambuscus nigra*), common vervain (*Verbena officinalis*), angelica (*Angelica archangelica*), birthwort (*Aristolochia clematitis*), alder (*Aulnus glutinosa*), southerwood (*Artemisia abrotanum*), bistort (*Polygonum bistorta*), birch (*Betula alba*), blessed thistle (*Onicus benedictus*), juniper (*Juniperus communis*), medlar (*Nespilus germanica*), blue-gum (*Eucalyptus globulus*), lady's fingers (*Anthyllis vulnerara*), herb-bennet (*Geum urbanum*), star thistle (*Centaurea calcitrapa*), cabbage (*Brassica oleracea*), houseleek (*Sempervivum tectorum*), strawberry (*Fragaria vesca*), horsetail (Equisetum spp), meadowsweet (*Spiraea ulmaria*), colt's-foot (*Tussilage iarfara*) pansy (Viola spp), burdock (*Arctium majus*), daisy (*Bellis perennis*) and white lily (*Lilium candidum*), (9) those plants exhibiting tonic properties include wormwood (*Artemisia absinthium*), arnica (*Arnica montana*), calamint (*Calamentha officinalis*), cinnamon-tree (Cinnamonum spp), geranium (Geranium spp), hyssop (*Hysopus officinalis*), marjoram (*Majorana hortensis*), balm (*Melissa officinalis*), parsley (*Petroselenium hortense*), pine-tree (Pinus spp), sylvestre, rosemary (*Rosmarinus officinalis*), savory (*Satureia hortensis*), serpollet (*Thymus serpyllum*), basil (*Ocimum basilicum*), dog rose (*Rosa canina*), gentian (*Gentiana lutea*), hops (*Humulus lupulus*), white laurel, mint (Mentha spp), sage (*Salvia officinalis*), tormentil (*Potentilla tormentilla*), yarrow (*Achillea millefolium*), agrimony (*Agrimonia eupatoria*), herb-bennet (*Geum urbanum*), bistort (*Polygonum bistorta*), chestnut tree (Quercus spp), quince (*Cyclonia vulgaris*), evergreen cypress (*Cupressus sempervirens*), horsechestnut (*Aesculus hippocastanum*), medlar (*Nespilus germanica*), walnut tree (Juglon spp), nettle (Urtica spp), plantain (Plantago spp), water pepper (*Polygonum hydropiper*), cinquefoil (*Potentille reptans*), bloodwort (*Polygonum aviculare*), grass-polly (*Lythrum salicaria*), speedwell (*Veronica officinalis*), angelica (*Angelica archangelica*), mugwort (*Artemisia vulgaris*), sweet woodruff (*Asperula odorata*), juniper (*Juniperus communis*), black mustard (*Brassica nigra*), cinchona (Cinchona spp), fumitory (*Fumaria officinalis*), large indian cress (*Tropeolum majus*), water-cress (*Nasturtium officinale*), bladder wrack (*Fucus vesiculosus*), butcher's broom (*Ruscus aculeatus*) and tansy (*Tanatecum vulgare*),

(10) those plants capable of imparting a color to the compositions containing them or capable of coloring the keratin of the hair or skin include henna (*Lawsonia inermis*), walnut tree (Juglon spp), wild chamomile (*Matricaria chamomilla*), rhubarb (Rhuem spp), bedstraw (Gallium spp), madder (*Rubia tinctorium*), sweet woodruff (*Asperula odorata*), alkannet (*Alkanna tinctoria*), roselle (Hibiscus spp), safflower (*Carthamus tinctorius*), indigo (*Indigofera tinctoria*), red sandalwood (Pterocarpus spp), dogwood (*Hematoxylon campechianum*), brazilwood (Caesalpinia spp), weld (*Reseda luteola*), sumac (Rhus spp), bloodroot (*Sanguinaria canadiensis*), saffron (*Crocus sativus*), arrow root (Curcuma spp), annata (*Bixa orellana*), lichen (Parmella spp or Rocella spp), broom (*Cytisus scoparius*), marigold (Tagetes spp), black-thorn (*Prunus spinosa*), elder (*Sambuscus nigra*), goldenrod (*Solidago Virga aurea*), strawberry tree (*Arbutus unedo*), privet (*Ligustrum vulgare*), alder (*Aulnus glutinosa*), garden peony (*Paeonia officinalis*), gilower (*Dianthus caryophyllus*), red poppy (*Papaver rhoeas*), marigold (*Calandula officinalis*), French rose (*Rose gallica*), pansy (Viola spp), cornflower (*Centaurea cyanus*), acacia (*Robinia pseudoacacia*), Mallow (Malva spp), sweet orange tree (*Citrus aurantium*), lucern (*Medicago sativa*), spinach (*Spinacia oleracea*), black currant (*Ribes nigrum*), beet (*Beta vulgaris*), rough cherry (*Prunus cerasus*), carrot (*Daucus carota*) and red quebracho (*Loxoterygium lorentzi*).

The pulverized plant powder must be present in the compositions of the present invention an an amount such that the composition has good viscosity. This is generally achieved when the particles are present in an amount greater than or equal to 5 weight percent, and preferably, between 5 and 30 weight percent relative to the total weight of the composition.

The cohesion agent capable of maintaining homogeneity of the composition is, in particular, (1) a solvent, such as
(i) monoalcohols and, principally an alkanol having between 1 and 8 carbon atoms such as ethanol, isopropanol, benzyl alcohol or phenylethyl alcohol,
(ii) polyalcohols and, principally, alkylene glycols such as ethylene glycol, propylene glycol and glycerol.
(iii) glycol ethers and, principally, the mono-, di- and tri ethylene glycol mono alkyl ethers, such as ethyleneglycolmonoethyl ether and diethyleneglycolmonoethyl ether,
(iv) esters and, principally,
the acetate of monomethylether of ethylene glycol and the acetate of monoethyl ether of ethyleneglycol, and
(v) esters of fatty acids and lower alcohols such as isopropyl myristate or isopropyl palmitate, used alone or in admixture;

(2) fatty bodies such as mineral oils, animal oils, vegetable oils, synthetic oils, triglycerides of synthetic fatty acids, fatty alcohols, esters of fatty acids used alone or in admixture.

Representative mineral oils include petrolatum oil.

Representative animal oils include whale oil, seal oil, menhaden oil, halibut liver oil, cod liver oil, tuna oil, tallow oil, beef oil, horse oil, sheep oil, mink oil, otter oil, hog oil and lanolin.

Representative vegetable oils include almond oil, peanut oil, wheat germ oil, linseed oil, apricot pit oil, walnut oil, palm oil, pistachio oil, sesame oil, poppy oil, pine oil, ricin oil, soy oil, avocado oil, safflower oil, coconut oil, hazelnut oil, olive oil, grape seed oil, turnsol oil, colza oil, cade oil, corn germ oil, peach pit oil, coffee oil, jojoba oil and the like.

Representative triglycerides of synthetic fatty acids include the triglycerides of fatty acids having 6 to 12 carbon atoms.

Representative fatty alcohols include unsaturated alcohols such as oleic alcohol or saturated alcohols such as 2-octyldodecanol.

Representative esters of fatty acids include the isopropyl esters of myristic acid, palmitic acid and stearic acid.

There can also be employed as a fatty body, a wax such as Carnauba wax, Candellila wax or beeswax.

(3) Thickening agents such as:
(i) vegetable thickening agents soluble in water such as gum arabic, karaya gum, xanthane gum, gum tragacanth, guar gum, carob seed gum, tara gum, pectines, alginates, carraghenates, agar-agar, furcellaria, starches, the water soluble portions of mucilagenous plants such as those of mullein, wild chamomile, fenugreck, marsh mallow, mallow, linen, lime tree, fleawort, plantain, borage, star thistle, alder buckthorn, large blackroot, asparagus, senna and lichen,
(ii) cellulose derivatives such as: methylcellulose, hydroxymethylcellulose, hydroxyethylcellulose and hydroxypropylcellulose,
(iii) synthetic polymers such as sodium polyacrylate, polyvinyl alcohol, carboxylic polymers derived from acrylic acid such as the CARBOPOLS, ether derivatives of cellulose such as JR 125, JR 400 and JR 30 M, sold by Union Carbide and cationic polysaccharides such as JAGUAR C 13S sold by Meyhall, and
(iv) mineral thickening agents such as: compounds of silicon, silicates, silica, clays (montmorillonite, attapulgite, kaolite, zeolite, etc)

(4) Emulsifying agents of the anionic, cationic or non-ionic type.

Representative anionic emulsifiers include alkali and alkaline earth soaps such as sodium stearate or calcium oleate, soaps of organic bases, salts of sulfated or sulfonated derivatives oxyethylenated or not, such as sodium lauryl sulfate.

Representative cationic emulsifiers include quaternary ammonium salts, such as benzalkonium chloride and cetyl pyridinium chloride.

Representative non-ionic emulsifiers include, in particular, aliphatic fatty alcohols such as cetyl alcohol or stearyl alcohol or a mixture of the two, fatty alcohols or α-diols oxyethylenated or polyglycerolated such as oleyl alcohol polyoxyethylenated with 10 moles of ethylene oxide, 1,2-octadecanediol polyglycerolated with 2 to 7 moles of glycidol, cyclic fatty alcohols, glycol esters of fatty acids such as ethyleneglycol stearate, the mono- or di-stearates of glycerol, the polyethyleneglycol esters of fatty acids such as polyethyleneglycol stearates, the fatty esters of sorbitan oxyethylenated or not and sold under the tradename of Tweens or Spans by Atlas, the fatty esters of sucrose, the fatty esters of glucose derivatives such as methylglucoside sesquistearate and methylglucoside sesquistearate polyoxyethylenated with 20 moles of ethylene oxide, and (5) an emulsion which can be of the oil-in-water or water-in-oil type.

The oil phase of the emulsion in accordance with the present invention can be selected from a large variety of products such as:
(i) hydrocarbon oils such as paraffin oil, Purcellin oil, perhydrosqualene and solutions of microcrystalline wax in oil,
(ii) animal or vegetable oils such as sweet almond oil, avocado oil, callophylum oil, lanolin, ricin oil, horse oil, hog oil and olive oil,
(iii) mineral oils whose initial distillation point at atmospheric pressure is about 250° C. and whose final distillation point is in the order of 410° C., and
(iv) saturated esters such as isopropyl palmitate, alkyl myristates such as those of isopropyl, butyl and cetyl, hexadecyl stearate, ethyl palmitate, the triglycerides of octanoic and decanoic acids and cetyl ricinoleate.

If desired, there can be added to the "oil" phase silicone oils soluble in other oils, such as dimethylpolysiloxane and methylphenylsiloxane.

To assist oil retention there can be used waxes such as Carnauba wax, Candellila wax, beeswax, microcrystalline wax and ozokerite.

The compositions according to the present invention can also contain various cosmetic adjuvants such as pH modifiers, perfumes, dyes or pigments, preservative agents, antioxidants, sequesterants or sun screen agents.

The compositions according to the invention can also contain plant extracts such as those of burdock or even powders of exhausted plants.

When the compositions of the present invention are to be used in the treatment of the skin, these compositions can be provided in the form of creams, milks, gels, makeup for the eyelids or cheeks, masks for the skin, lipstick, depilatory compositions, bath products, deodorant powders, antiperspirant powders and aftershave products.

When the compositions according to the invention are more particularly to be used for the treatment of the skin, the plant particles can originate from plants having astringent, anti-inflammatory, antiseptic, anti-pruriginous, cicatrisive, tonic, emollient or soothing characteristics.

The masks of the present invention effect a cleansing or an in depth treatment of the face, and are provided in various forms, principally as a paste, as a powder to be made into a paste or as an emulsion. After application to the face, the composition is permitted to dry and is then finally rinsed off with water.

The masks according to the invention contain powders having a granulometry ≦125 mixrons and preferably ≦80 microns originating from the pulverization of plants having emollient, anti-pruriginous, antiseptic, tonic or astringent characteristics, combined with a cohesion agent selected preferably from a thickening agent or an emulsion.

To enhance their activity they can additionally contain synthetic or natural active principles.

When the compositions according to the present invention are provided in the form of make-up products, they contain a powder such as defined above originating from colored plants, this powder being combined with a fatty body, a thickening agent or an emulsion as the cohesion agent.

It is to be understood that these compositions can also contain cosmetically acceptable dyes or pigments which have the effect of reinforcing or varying the colors obtained.

When the compositions according to the invention are to be used for the treatment of the hair, they can be provided in the form of shampoos, dye products, rinse treatment products to be applied before or after a shampoo, a dye, a bleach, a permanent wave composition or a hair uncurling composition.

These compositions which are to be used for the treatment of the hair or skin can also be packaged in aerosol containers together with a propellant gas.

The following non-limiting examples illustrate the compositions of the present invention.

EXAMPLE 1

| | |
|---|---|
| Powder of the flower of mallow having a granulometry ≦125 microns | 13.7 g |
| Turnsol oil | 7.8 g |
| Preservative, sufficient amount | |
| Water, sufficient amount for | 100.0 g |

This product has the appearance of a cream and is applied to clean hair. After 15 minutes of contact, the hair is rinsed. The hair is soft and shiny.

EXAMPLE 2

| | |
|---|---|
| Powder of the flowers of barbary fig having a granulometry of ≦80 microns | 14.3 g |
| Turnsol oil | 35.7 g |
| Preservative, sufficient amount | |
| Water, sufficient amount for | 100.0 g |

This product has the appearance of a cream that is applied to wet hair.

After 20 minutes of contact, the hair is rinsed and then shampooed. The hair thus treated is soft and shiny.

EXAMPLE 3

| | |
|---|---|
| Powder of the flowers of acacia having a granulometry ≦80 microns | 40.0 g |
| Preservative, sufficient amount | |
| Turnsol oil, sufficient amount for | 100.0 g |

This composition having the appearance of a cream is applied to the hair.

After 20 minutes of contact time, the hair is rinsed and then shampooed. The hair thus treated is firm and shiny.

EXAMPLE 4

| | |
|---|---|
| Powder of the flowers of mallow having a granulometry ≦80 microns | 17.0 g |
| Glycerin | 40.0 g |
| Preservative, sufficient amount | |
| Water, sufficient amount for | 100.0 g |

This composition when applied to clean hair and rinsed after a contact time of 20 minutes, imparts much softness to the hair.

EXAMPLE 5

Thinning Body Cream

| | |
|---|---|
| Powder of the vesiculose bladder wrack having a granulometry ≦120 microns | 5.0 g |
| Powder of cut quick grass or cut Bermuda grass roots having a granulometry between 50 and 120 microns | 10.0 g |
| Propylene glycol | 7.0 g |
| Polyethylene glycol 400 | 3.0 g |
| Triethanolamine | 0.6 g |
| Stearic acid | 3.0 g |
| Mixture of glycerol mono- and di-stearates | 3.0 g |
| Cetyl alcohol | 3.0 g |
| Isopropyl myristate | 2.0 g |
| Sweet almond oil | 2.0 g |
| Antioxidant | 0.05 g |
| Preservative | 0.3 g |
| Perfume | 0.5 g |
| Water, sufficient amount for | 100.0 g |

EXAMPLE 6

Thinning Body Cream

| | |
|---|---|
| Powder of vesiculose bladder wrack having a granulometry ≦120 microns | 5.0 g |
| Powder of cut quick grass or cut Bermuda grass roots having a granulometry between 50 and 120 microns | 10.0 g |
| Propylene glycol | 7.0 g |
| Polyethylene glycol 400 | 3.0 g |
| Triethanolamine | 0.6 g |
| Stearic acid | 3.0 g |
| Mixture of glycerol mono- and di-stearates | 3.0 g |
| Cetyl alcohol | 3.0 g |
| Isopropyl myristate | 2.0 g |
| Sweet almond oil | 2.0 g |
| Bile salts (mixture of pure sodium taurocholate and glycocholate, sold by Prolabo) | 0.5 g |
| Antioxidant | 0.05 g |
| Preservative | 0.3 g |
| Perfume | 0.5 g |
| Demineralized water, sufficient amount for | 100 g |

EXAMPLE 7

Rinse Mask for Dry Skin

| | |
|---|---|
| Powder of the roots of marsh mallow having a granulometry ≦ 80 microns | 20.0 g |
| Propylene glycol | 12 g |
| Titanium dioxide | 0.5 g |
| Food grade gelatin | 1.0 g |
| Mucilage from plantain seeds | 1.0 g |
| Preservative, sufficient amount | |
| Water, sufficient amount for | 100 g |

EXAMPLE 8

Rinse Mask for Dry Skin in Emulsion Form

| | |
|---|---|
| Powder of fenugreek having a granulometry ≦ 80 microns | 12.0 g |
| Arlacel 165 (glycerine monostearate) | 5 g |
| Triple pressed stearic acid | 2 g |
| Tween 60 (sorbitan monostearate oxyethylenated with 20 moles of ethylene oxide) | 1.5 g |
| Cetyl alcohol | 0.8 g |
| Petrolatum oil | 18.0 g |
| Tween 20 (sorbitan monolaurate oxyethylenated with 20 moles of ethylene oxide) | 2.0 g |
| Glycerin | 7.0 g |
| Mucilage from plantain seeds | 0.9 g |
| Preservative, sufficient amount | |
| Perfume, sufficient amount | |
| Water, sufficient amount for | 100 g |

EXAMPLE 9

Soothing Cream in Emulsion Form

| | |
|---|---|
| Powder of juniper having a granulometry ≦ 80 microns | 14.0 g |
| Triglycerides of saturated fatty acids sold under the trade name Miglyol 812 by Dynamit Nobel | 4.0 g |
| Cetyl alcohol | 0.5 g |
| Decyl ester of oleic acid | 5.0 g |
| Petrolatum oil | 13.0 g |
| Polyglycol ether of cetyl alcohol oxyethylenated with 10 moles of ethylene oxide | 4.0 g |
| Perfume, sufficient amount | |
| Preservative, sufficient amount | |
| Water, sufficient amount for | 100 g |

EXAMPLE 10

Soothing Gel

| | |
|---|---|
| Powder of lettuce leaves having a granulometry ≦ 80 microns | 13.0 g |
| Propylene glycol | 10.0 g |
| Carbopol 940 | 0.8 g |
| Sorbitan monolaurate polyoxyethylenated | 0.5 g |
| Ethylenediamine tetraacetic acid | 0.05 g |
| Triethanolamine | 1.0 g |
| Methyl parahydroxybenzoate, sufficient amount | |
| Perfume, sufficient amount | |
| Preservative, sufficient amount | |
| Water, sufficient amount for | 100 g |

EXAMPLE 11

Cream for Oily Skin Having Acne Tendencies

| | |
|---|---|
| Powder of sage leaves having a granulometry ≦ 80 microns | 15.0 g |
| Myrj 49 (stearate polyoxyethylenated with 20 moles of ethylene oxide) | 6.6 g |
| Mixture of glycerol mono- and di-stearates, non self-emulsifiable | 1.2 g |
| Cetyl alcohol | 4.2 g |
| Mixture of cetylstearyl alcohol and sodium alkylsulfate | 4.0 g |
| Petrolatum oil | 5.0 g |
| Cyclic dimethylpolysiloxane | 5.0 g |
| S—carboxymethyl cysteine | 1.0 g |
| Triethanolamine, sufficient for pH = 6.8 | |
| Preservative | 0.3 g |
| Perfume | 0.3 g |
| Water, sufficient amount for | 100 g |

EXAMPLE 12

Mask in Cream Form

| | |
|---|---|
| Powder of lady's mantle leaves having a granulometry ≦ 80 microns | 2.0 g |
| Simulsol 165 (glycerol monostearate and oxyethylenated emulsifier) | 4.5 g |
| Stearin | 3.5 g |
| Tween 60 | 2.5 g |
| Cetyl alcohol | 1.0 g |
| Petrolatum oil | 20.0 g |
| Triethanolamine | 1.0 g |
| Starch | 15.0 g |
| Glycol extract of burdock | 10.0 g |
| Preservative, sufficient amount | |
| Perfume, sufficient amount | |
| Water, sufficient amount for | 100 g |

In this example, the burdock extract can be replaced by a tincture of large indian cress or an extract of water cress.

EXAMPLE 13

Rinse Mask

| | |
|---|---|
| Powder of pine tree having a granulometry ≦ 125 microns | 25.0 g |
| Propylene glycol | 15 g |
| Titanium dioxide | 1 g |
| Gelatin | 1 g |
| Mucilage from plantain seeds | 0.7 g |
| Preservative, sufficient amount | |
| Perfume, sufficient amount | |
| Water, sufficient amount for | 100 g |

EXAMPLE 14

Body Cream

| | |
|---|---|
| Powder of black root having a granulometry ≦ 80 microns | 8.00 g |
| Magnesium lanolate | 2.85 g |
| Lanolin alcohol | 6.65 g |
| Isopropyl palmitate | 22.20 g |
| Paraffin oil | 26.00 g |
| Sweet almond oil | 0.30 g |
| Ozokerite | 2.00 g |
| Silicone oil | 2.00 g |
| Preservative, sufficient amount | |
| Water, sufficient amount for | 100 g |

EXAMPLE 15

Astringent Mask for Oily Skin

| | |
|---|---|
| Powder of witch hazel leaves having a granulometry ≦ 10 microns | 15 g |
| Food grade gelatin | 3 g |
| Wheat starch | 15 g |
| Titanium oxide | 14 g |
| Lemon pectin | 8 g |
| Exhausted and micronized powder of horse chestnut, sufficient amount for | 100 g |

10 g of the above powder are diluted with 20 to 30 g of water so as to obtain a pasty consistency applicable with a spatula.

EXAMPLE 16

Anhydrous Lipstick

| | |
|---|---|
| Powder of the flowers of rose having a granulometry ≦ 80 microns | 5.0 g |
| Ozokerite | 14.4 g |
| Lanolin | 23.0 g |
| Oleyl alcohol | 8.9 g |
| Cetyl ricinoleate | 15.8 g |
| Triglycerides of octanoic acid | 16.8 g |
| Oil of wheat germ | 1.0 g |
| Copolymer of vinyl acetate/allyl stearate (MW = 10,000) | 4.5 g |
| Butyl hydroxyanisole | 0.1 g |
| U.V. filter | 1.0 g |
| Perfume, sufficient amount | |
| Dyes, optional, sufficient amount | |

EXAMPLE 17

Rinse Mask

| | |
|---|---|
| Powder of horsetail having a granulometry ≦ 80 microns | 13 g |
| Arlacel 165 | 5 g |
| Triple pressed stearic acid | 2 g |
| Tween 60 | 1.5 g |
| Cetyl alcohol | 1 g |
| Petrolatum oil | 18 g |
| Tween 20 | 2.2 g |
| Glycerin | 8 g |
| Mucilage from plantain seeds | 0.8 g |
| Preservative, sufficient amount | |
| Perfume, sufficient amount | |
| Water, sufficient amount for | 100 g |

EXAMPLE 18

Firming Cream

| | |
|---|---|
| Powder of the lady's mantle leaves having a granulometry ≦ 80 microns | 2.0 g |
| Powder of bistort rhizomes having a granulometry ≦ 80 microns | 3.0 g |
| Myrj 49 | 1.0 g |
| Stearic acid | 1.0 g |
| Mixture of glycerol mono- and di-stearates, non self-emulsifiable | 8.0 g |
| Perhydrosqualene | 4.5 g |
| Isopropyl myristate | 8.0 g |
| Petrolatum oil | 12.0 g |
| Allantoin | 0.7 g |
| Preservative | 0.3 g |
| Perfume | 0.3 g |
| Water, sufficient amount for | 100 g |

EXAMPLE 19

Nacreous Eyelid Make-up in Compacted Powder Form

| | |
|---|---|
| Powder of lucern leaves having a granulometry ≦ 80 microns | 20 g |
| Talc | 25 g |
| Nylon powder | 1 g |
| Zinc stearate | 3 g |
| Titanium oxide | 2 g |
| Mica-titanium | 20 g |
| Bismuth oxychloride | 10 g |
| Ultramarine blue | 1 g |
| Anhydrous chrome oxide | 6 g |
| Mineral oil | 3 g |

EXAMPLE 20

Free Powder for the Eyelids

| | |
|---|---|
| Powder of the flowers of red poppy having a granulometry ≦ 80 microns | 10 g |
| Titanium oxide | 1 g |
| Starch | 20 g |
| Kaolin | 2 g |
| Magnesium stearate | 2 g |
| Magnesium carbonate | 1 g |
| Isopropyl myristate | 0.5 g |
| Perfume | 0.8 g |
| Talc, sufficient amount for | 100 g |

EXAMPLE 21

Eyelid Make-up in Emulsion Form

| | |
|---|---|
| Powder of spinach leaves having a granulometry ≦ 80 microns | 5 g |
| Powder of the fruit of black currant having a granulometry ≦ 80 microns | 10 g |
| Magnesium lanolate | 3.8 g |
| Hydrogenated lanolin | 5.7 g |
| Ozokerite | 15 g |
| Isopropyl palmitate | 10 g |
| Paraffin oil | 13.5 g |
| Titanium oxide | 2 g |
| Propyl parahydroxybenzoate, sufficient amount | |
| Water, sufficient amount for | 100 g |

EXAMPLE 22

Eyelid Make-up in Anhydrous Cream Form

| | |
|---|---|
| Powder of the flowers of mallow having a granulometry ≦ 80 microns | 15 g |
| Coco butter | 2 g |
| Beeswax | 3 g |
| Spermaceti | 5 g |
| Lanolin | 5 g |
| Petrolatum | 50 g |
| Zinc oxide | 15 g |
| Dyes | 4 g |
| Preservative | 1 g |

EXAMPLE 23

Cheek Make-up in Anhydrous Cream Form

| | |
|---|---|
| Powder of the flowers of roselle having a granulometry ≦ 80 microns | 12.0 g |

-continued

| | |
|---|---|
| Ozokerite | 9 g |
| Carnauba wax | 2 g |
| Candelilla wax | 2 g |
| Hydrogenated lanolin | 4.8 g |
| Ricin oil | 30 g |
| Oleyl alcohol | 14.5 g |
| Isopropyl lanolate | 10.2 g |
| Liquid lanolin | 4.8 g |
| Vinyl polystearate (MW = 34,000) | 9.6 g |
| Butylhydroxytoluene | 0.1 g |
| Perfume | 1 g |

EXAMPLE 24

Cheek Make-up in Emulsion Form

| | |
|---|---|
| Powder of the roots of red beets having a granulometry ≦80 microns | 12.0 g |
| Stearic acid | 15.0 g |
| Propylene glycol monostearate | 2.5 g |
| Isopropyl myristate | 2.0 g |
| Tween 60 | 1.5 g |
| Propylene glycol | 10.0 g |
| Perfume, sufficient amount | |
| Preservative, sufficient amount | |
| Water, sufficient amount for | 100 g |

EXAMPLE 25

Cheek Make-up in Free Powder Form

| | |
|---|---|
| Powder of the flowers of red poppy having a granulometry 80 microns | 5 g |
| Talc | 50 g |
| Kaolin | 10 g |
| Rice Starch | 10 g |
| Zinc oxide | 14 g |
| Zinc stearate | 7 g |
| Perfume, sufficient amount | |
| Dye, sufficient amount | |

EXAMPLE 26

Cheek Make-up in Compacted Powder Form

| | |
|---|---|
| Powder of the fruit of cherry having granulometry ≦ 125 microns | 7 g |
| Powder of annata seeds having a granulometry ≦ 125 microns | 3 g |
| Talc | 60 g |
| Kaolin | 15 g |
| Titanium oxide | 3 g |
| Zinc stearate | 5 g |
| Perfume | 1 g |
| Binder - | |
| Gum tragacanth | 0.12 g |
| Glucose | 0.3 g |
| Water + Preservative | 5.58 g |
| | 100 g |

EXAMPLE 27

Complexion Foundation in Emulsion Form

| | |
|---|---|
| Powder of the roots of arrow root having a granulometry ≦ 80 microns | 7.00 g |
| Powder of red sandalwood having a granulometry ≦ 125 microns | 8.00 g |
| Stearic acid | 1.35 g |
| Propylene glycol monostearate | 3.95 g |
| Lanolin | 1.05 g |
| Mineral oil and lanolin alcohols (Amerchol L 101) | 2.65 g |
| Mineral oil | 12.20 g |
| Propyl parahydroxybenzoate | 0.05 g |
| Triethanolamine | 0.20 g |
| Propylene glycol | 5.30 g |
| Sodium salt of carboxymethylcellulose | 0.25 g |
| Methyl parahydroxybenzoate | 0.10 g |
| Titanium oxide | 8.30 g |
| Colloidal kaolin | 5.10 g |
| Sodium lauryl sulfate | 0.80 g |
| Talc | 0.35 g |
| Silicate of magnesium and aluminum | 1.10 g |
| Perfume | 1 g |
| Water, sufficient amount for | 100 g |

EXAMPLE 28

Complexion Foundation in Aqueous Gel Form

| | |
|---|---|
| Powder of the roots of carrots having a granulometry ≦ 80 microns | 10.0 g |
| Propylene glycol | 10.0 g |
| Carbopol 940 | 0.8 g |
| Sorbitan monolaurate polyoxyethylenated with 20 moles of ethylene oxide | 0.5 g |
| Ethylene diamine tetraacetic acid | 0.05 g |
| Triethanolamine | 1.0 g |
| Mica-titanium | 3.0 g |
| Dyes, sufficient amount | |
| Methyl parahydroxybenzoate, sufficient amount | |
| Perfume, sufficient amount | |
| Water, sufficient amount for | 100 g |

EXAMPLE 29

Complexion Foundation in Hydroalcoholic Gel Form

| | |
|---|---|
| Powder of red quebracho having a granulometry ≦ 125 microns | 10.00 g |
| Powder of saffron stigmas having a granulometry ≦ 80 microns | 5.00 g |
| Ethyl alcohol | 24.45 g |
| Carbopol 940 (3% solution) | 31.45 g |
| Hexylene glycol | 1.95 g |
| Glycerol | 1.95 g |
| Tween 20 | 2.95 g |
| Diisopropanolamine (10% solution) | 7.80 g |
| Unival 400 (2,4-dihydroxybenzophenone) | 0.05 g |
| Diisopropyl adipate | 1.95 g |
| Pigments | 1.25 g |
| Perfume, sufficient amount | |
| Water, sufficient amount for | 100 g |

EXAMPLE 30

Lipstick

| | |
|---|---|
| Powder of red sandalwood having a granulometry ≦ 125 microns | 5 g |
| Ozokerite | 14.4 g |
| Lanolin | 23.0 g |
| Oleyl alcohol | 8.9 g |
| Cetyl ricinoleate | 15.8 g |
| Triglycerides of octanoic acid | 16.8 g |
| Wheat germ oil | 1.0 g |
| Copolymer of vinyl acetate/allyl stearate (MW = 10,000) | 4.5 g |
| Butylhydroxyanisole | 0.1 g |
| U.V. filter | 1.0 g |
| Perfume, sufficient amount | |

EXAMPLE 31

Mask For Skin Subject to Acne

| | |
|---|---|
| Powder of horsechestnut having a granulometry ≦ 125 microns | 18 g |
| Arlacel 165 | 4 g |
| Stearic acid | 2 g |
| Tween 60 | 0.8 g |
| Cetyl alcohol | 1 g |
| Petrolatum oil | 20 g |
| Tween 20 | 2.5 g |
| Propylene glycol | 7 g |
| Horsechestnut extract | 4 g |
| Mucilages of plantain seeds | 0.8 g |
| Preservative, sufficient amount | |
| Perfume, sufficient amount | |
| Water, sufficient amount for | 100 g |

EXAMPLE 32

After shave lotion

| | |
|---|---|
| Powder of bistort roots having a granulometry ≦ 80 microns | 5 g |
| Carboxyvinyl polymer sold under the gradename Carbopol 940 by Goodrich Chemical | 0.04 g |
| Ethyl alcohol sufficient amount for | 55° |
| Allantoin | 0.1 g |
| Water, sufficient amount for | 100 cc |

EXAMPLE 33

Deodorant Milk

| | |
|---|---|
| Powder of rosemary leaves having a granulometry ≦ 80 microns | 5 g |
| Sorbitan sesquioleate | 2 g |
| Glycerol stearate | 5 g |
| Lanolin | 1 g |
| Ethoxylated lanolin | 1 g |
| Hexamethyltetracosane | 5 g |
| Carboxyvinyl polymer sold under the tradename CARBOPOL 940 by Goodrich Chemical | 0.5 g |
| Triethanolamine, sufficient amount for pH = 7 | |
| Ethyl alcohol | 10 g |
| Irgasan DP 300 (2,4,4'-trichloro-2'-hydroxydiphenyl ether) | 0.3 g |
| Perfume | 0.5 g |
| Water, sufficient amount for | 100 g |

EXAMPLE 34

Antiperspirant Cream

| | |
|---|---|
| Powder of chestnut tree having a granulometry ≦ 125 microns | 5 g |
| Glycerol stearate, self-emulsifiable | 6 g |
| Stearic acid | 2 g |
| Ricin oil | 2 g |
| Petrolatum oil | 5 g |
| Isopropyl myristate | 3 g |
| Allantoin | 0.3 g |
| Aluminum chlorhydroxide | 10 g |
| Triethanolamine | 0.1 g |
| Water, sufficient amount for | 100 g |

EXAMPLE 35

Soothing Milk (After-sun)

| | |
|---|---|
| Powder of the fruit of passion flower having a granulometry ≦ 80 microns | 5 g |
| Sipol wax (30/70 cetyl stearyl alcohol) | 5 g |
| Petrolatum oil | 6 g |
| Isopropyl myristate | 3 g |
| Silicone oil | 1 g |
| Cetyl alcohol | 1 g |
| Glycerine | 10 g |
| Allontoin | 0.4 g |
| Callophylum oil | 0.2 g |
| Preservative, sufficient amount | |
| Perfume | 0.2 g |
| Water, sufficient amount for | 100 g |

EXAMPLE 36

Anhydrous stick

| | |
|---|---|
| Powder of the flowers of meadowsweet having a granulometry ≦ 80 microns | 5.0 g |
| Coco butter | 15.9 g |
| Ozokerite wax | 23.7 g |
| Paraffin | 7.9 g |
| Petrolatum | 15.9 g |
| Antioxidants, sufficient amount | |
| Perfume, sufficient amount | |
| Isopropyl myristate | 31.6 g |

What is claimed is:

1. A cosmetic composition for the hair or skin comprising from 5 to 30 percent by weight based on the total weight of said composition of pulverized particles of a plant having skin emollient and hair softening properties, said plant being selected from the group consisting of cornflower, fenugreck, barbary fig and linen, said particles having a granulometry equal to or lower than 80 microns and a cohesion agent present in an amount sufficient to maintain the homogeneity of said composition, said cohesion agent being a solvent, a fatty body, a thickening agent, an emulsifier, an emulsion or a mixture thereof.

2. The cosmetic composition of claim 1, wherein said plant is barbary fig.

3. A method for treating the hair or skin so as to impart thereto skin emollient or hair softening properties, said process comprising applying to said hair or skin an amount, effective to impart said properties to said hair or skin, of a composition comprising from 5 to 30 percent by weight based on the total weight of said composition of pulverized particles of a plant selected from the group consisting of cornflower, fenugreek, barbary fig and linen, said particles having a granulometry equal to or lower than 125 microns and a cohesion agent present in an amount sufficient to maintain the homogeneity of said composition, said cohesion agent being a solvent, a fatty body, a thickening agent, an emulsifier, an emulsion or a mixture thereof.

4. A method for imparting softening properties to hair comprising applying to said hair, in an amount effective to impart softening properties thereto, a composition comprising from 5 to 30 precent by weight, based on the total weight of said composition, of pulverized particles of a plant selected from the group consisting of red poppy, mallow and marsh mallow, said particles having a granulometry equal to or lower than 125 microns and a cohesion agent present in an amount sufficient to maintain the homogeniety of said composition, said cohesion agent being a solvent, a fatty body, a thickening agent, an emulsifier, an emulsion or a mixture thereof.

* * * * *